(12) United States Patent
Xing et al.

(10) Patent No.: US 11,647,968 B2
(45) Date of Patent: May 16, 2023

(54) DOOR ACCESS CONTROL SYSTEM WITH BODY TEMPERATURE DETECTION FUNCTION

(71) Applicant: NORTHWEST INSTRUMENT INC., Dover, NJ (US)

(72) Inventors: David Xing, Dover, NJ (US); Xin Shi, Shanghai (CN)

(73) Assignee: NORTHWEST INSTRUMENT INC., Dover, NJ (US)

( * ) Notice: Subject to any disclaimer, the term of this patent is extended or adjusted under 35 U.S.C. 154(b) by 59 days.

(21) Appl. No.: 17/094,119

(22) Filed: Nov. 10, 2020

(65) Prior Publication Data

US 2022/0031258 A1 Feb. 3, 2022

(30) Foreign Application Priority Data

Jul. 29, 2020 (CN) .......................... 202010742775.1
Oct. 23, 2020 (CN) .......................... 202011149714.0

(51) Int. Cl.

| | |
|---|---|
| *A61B 5/00* | (2006.01) |
| *G06T 7/70* | (2017.01) |
| *G07C 9/30* | (2020.01) |
| *A61B 5/01* | (2006.01) |
| *G01J 5/00* | (2022.01) |

(Continued)

(52) U.S. Cl.
CPC ............... *A61B 5/746* (2013.01); *A61B 5/01* (2013.01); *A61B 5/7246* (2013.01); *A61B 5/742* (2013.01); *A61B 5/7405* (2013.01); *G01J 5/0025* (2013.01); *G01J 5/025* (2013.01); *G01J 5/10* (2013.01); *G06T 7/70* (2017.01); *G07C 9/30* (2020.01); *G08B 21/02* (2013.01); *H04N 5/38* (2013.01); *H04N 5/76* (2013.01); *H04N 7/18* (2013.01); *H04R 1/028* (2013.01); *G06T 2207/30196* (2013.01); *G06T 2207/30242* (2013.01)

(58) Field of Classification Search
CPC ......................................................... A61B 5/01
USPC ......................................................... 340/573.1
See application file for complete search history.

(56) References Cited

U.S. PATENT DOCUMENTS

2006/0222237 A1* 10/2006 Du .......................... G01N 25/72
  382/152
2021/0304901 A1* 9/2021 Pal .......................... G16H 10/60
(Continued)

FOREIGN PATENT DOCUMENTS

CN 111225066 A 6/2020
CN 111311799 A 6/2020
(Continued)

OTHER PUBLICATIONS

European Patent Office European Search Report for Application No. EP21158560.9 dated Aug. 25, 2021 8 pages.

*Primary Examiner* — Fabricio R Murillo Garcia
(74) *Attorney, Agent, or Firm* — Anova Law Group, PLLC

(57) ABSTRACT

A door access control system with a temperature detection function includes an infrared body temperature monitor device configured to detect a body temperature of a monitored object; a body temperature comparison device configured to compare a detected body temperature of the monitored object with a body temperature threshold; and a warning device configured to issue a warning message in response to the detected body temperature of the monitored object being higher than the body temperature threshold.

19 Claims, 3 Drawing Sheets

(51) Int. Cl.
*G01J 5/02* (2022.01)
*G01J 5/10* (2006.01)
*G08B 21/02* (2006.01)
*H04N 5/38* (2006.01)
*H04N 5/76* (2006.01)
*H04N 7/18* (2006.01)
*H04R 1/02* (2006.01)

(56) References Cited

U.S. PATENT DOCUMENTS

2021/0369122 A1* 12/2021 Lane ................. G01J 5/0275
2021/0378519 A1* 12/2021 Akgun ................ G01K 13/20
2021/0390804 A1* 12/2021 Rajamanickam ...... A61B 5/742
2022/0012894 A1* 1/2022 Lev .................. G06V 40/166

FOREIGN PATENT DOCUMENTS

| CN | 111311803 A | 6/2020 |
| CN | 111369722 A | 7/2020 |
| KR | 20170083842 A | 7/2017 |
| WO | 2011005224 A1 | 1/2011 |

\* cited by examiner

DOOR ACCESS CONTROL SYSTEM WITH BODY TEMPERATURE DETECTION FUNCTION

CROSS-REFERENCE TO RELATED APPLICATION

This application claims priority to Chinese Patent Application No. 202010742775.1, filed Jul. 29, 2020, and Chinese Patent Application No. 202011149714.0, filed Oct. 23, 2020, the entire contents of both of which are incorporated herein by reference.

TECHNICAL FIELD

The present disclosure generally relates to the door access control system and, more particularly to a door access control system with a body temperature detection function.

BACKGROUND

As the smart home technology gains popularity, a smart door access control system is gradually adopted to replace a cat eye camera and a conventional doorbell.

The existing smart door access control system used outdoors has a video recording function, a call function, and a data uploading function via a wireless communication module.

SUMMARY

Embodiments of the present disclosure provide a door access control system with a temperature detection function. The door access control system with a temperature detection function includes an infrared body temperature monitor device configured to detect a body temperature of a monitored object; a body temperature comparison device configured to compare a detected body temperature of the monitored object with a body temperature threshold; and a warning device configured to issue a warning message in response to the detected body temperature of the monitored object being higher than the body temperature threshold.

Other aspects of the present disclosure can be understood by those skilled in the art in light of the description, the claims, and the drawings of the present disclosure.

BRIEF DESCRIPTION OF THE DRAWINGS

The following drawings are merely examples for illustrative purposes according to various disclosed embodiments and are not intended to limit the scope of the present disclosure.

DETAILED DESCRIPTION OF THE EMBODIMENTS

In embodiments described in detail below, reference is made to accompanying drawings, which form a part of the present disclosure. The accompanying drawings show specific embodiments capable of implementing the present disclosure through examples. Exemplary embodiments are not intended to be exhaustive of all embodiments according to the present disclosure. Without departing from the scope of the present disclosure, other embodiments may be used, and structural or logical modifications may be made. Therefore, the following detailed description is not restrictive, and the scope of the present disclosure is defined by appended claims.

An existing smart door access control system may only have a function of using a camera to obtain an image. However, to address health issues, a user may require the smart door access control system to determine and record a body temperature of a visitor in addition to obtain and recognize a human face image. The existing smart door access control system does not have a function to measure and record the body temperature of the visitor.

Figure 1:
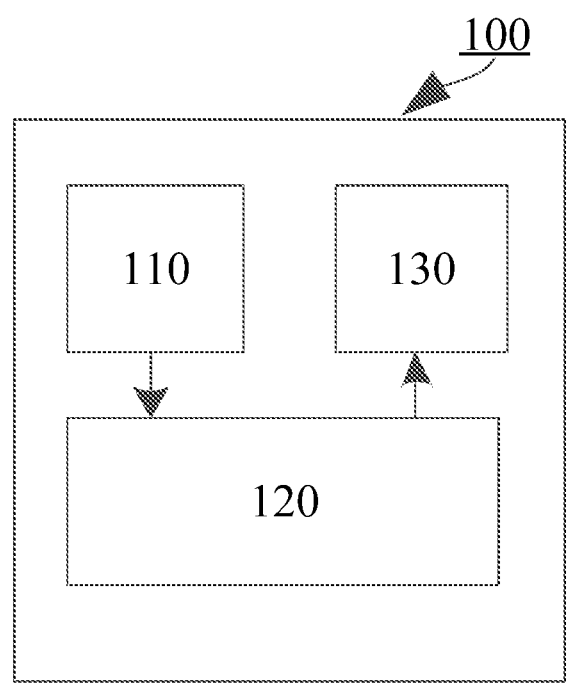
FIG. 1 is a schematic structural diagram of a door access control system with a body temperature detection function according to some embodiments of the present disclosure.

FIG. 1 is a schematic structural diagram of a door access control system 100 with the body temperature detection function according to some embodiments of the present disclosure. As shown in FIG. 1, embodiments of the present disclosure provide the door access control system 100 with the body temperature detection function.

First, the door access control system 100 with the body temperature detection function includes an infrared body temperature detection device 110. The infrared body temperature detection device 110 may be configured to detect the body temperature of a monitored object. With the infrared body temperature detection device 110, a body temperature of a human body close to the infrared body temperature detection device 110 may be detected to provide data support for subsequently monitoring the body temperature.

Then, the door access control system 100 with the body temperature detection function further includes a body temperature comparison device 120. The body temperature comparison device 120 may be configured to compare the detected body temperature of the monitored object with a predetermined body temperature threshold. For example, a visitor may have fever. The temperature of 37.3° C. is a general standard to determine the fever. Therefore, the predetermined body temperature threshold may be set to 37.3° C. Those of skill in the art should know that the 37.3° C. is merely exemplary not restrictive. Other body temperature thresholds related to other diseases may also be used.

Finally, the door access control system 100 with the body temperature detection function further includes a warning device 130. The warning device 130 may be configured to output a warning message when the detected body temperature of the monitored object is higher than the predetermined body temperature threshold.

The door access control system may be implemented in a form of a doorbell. For example, the doorbell may have a push button. After the visitor pushes the button, the owner may decide whether to open the door according to whether the door access control system such as the doorbell issues the warning message.

According to an embodiment according of the present disclosure, the door access control system may further include a query interface device. Those skilled in the art should understand that the query interface device may include a hardware interface, such as a USB or an HDMI connected to an external device for inputting query conditions. The query interface device may also be a software interface such as a graphical user interface, as long as it can implement the functionality of inputting query conditions and/or displaying query results. The query interface device may be configured to query information of visitors meeting predetermined conditions. For example, the information of visitor passing through the door access control system in a certain time period on a certain day or within a certain hour. For example, the predetermined condition may include a predetermined period of time, or below or above a predetermined temperature threshold. In further examples, the visitor information may include visitor images, time, number of people and/or body temperature.

According to certain embodiments, the door access control system may be used to query the information of visitors meeting predetermined conditions through its query interface device. For example, the query interface device may be used to query the number of people passing through the access control system on a certain day or within a certain hour. It may further be used to query the number of people having abnormal body temperature (e. g., above 37.3° C.) who passed through the access control system in a specific time period and their images. This information may provide reliable tracing or tracking data for disease prevention and control such as control of covid-19 epidemic. For example, the photo and body temperature of a person who meets the epidemiological tracking requirements may be exported by configuring the screening conditions. The CDC may use this information to find out that a patient has passed through the access control system, and thus providing necessary information support for timely isolation and so on. The image information may be combined with the facial recognition databases of the public security departments, so that the information tracked by epidemiologists may be accurately determined and used to reduce the further risk of the spread of infectious diseases.

The smart door access control system of embodiments of the present disclosure may have the body temperature measurement function. The smart door access control system may compare the detected body temperature of the monitored object with the predetermined body temperature threshold through the body temperature comparison device, and issue the warning message when the detected body temperature of the monitored object is higher than the predetermined body temperature threshold. As such, a contagious disease that may cause fever, may be effective prevented from spreading.

The warning device 130 may be implemented in various forms. For example, in some embodiments, the warning device 130 may include a visual reminder device. The visual reminder device may be configured to issue the warning message in a visual format. In some embodiments, the visual reminder device may include a display screen. Those of skill in the art should know that the visual reminder device, for example, may be a device capable of emitting light of different colors, a display screen capable of displaying different messages or signs, and/or an indicator capable of flashing lights in different sequences, etc., as long as the visual reminder device may indicate the warning message with different visual signs or optical signals.

In some embodiments, the display screen may include a touch screen, which may realize a dual interaction function. Further, an under-screen fingerprint recognition function may be integrated into the display screen, which may recognize the identity of the visitor through the under-screen fingerprint recognition function. In some embodiments, the visual reminder device may include a red indicator or a green indicator. When the detected body temperature of the monitored object is higher than the predetermined body temperature threshold, the red indicator may be lighted up, and the green indicator may not be lighted up. In some other embodiments, when the detected body temperature of the monitored object is not higher than the predetermined body temperature threshold, the red indicator may not be lighted up, and the green indicator may be lighted up. Therefore, a warning signal generated by the warning device 130 may be simply displayed in the forms of the red indicator or the green indicator, such that the door access control system of embodiments of the present disclosure may be easy to use and user friendly.

In addition, in some other embodiments, the warning device 130 may be, for example, a loudspeaker. The loudspeaker may be configured to issue an alarm buzzer or an alarm voice when the detected body temperature of the monitored object is higher than the predetermined body temperature threshold. Accordingly, the warning signal generated by the warning device 130 may be simply demonstrated in the forms of the alarm buzzer or the alarm voice, such that the door access control system of embodiments of the present disclosure may be easy to use and user friendly. In addition, the door access control system may include a microphone to realize a voice call function.

In addition, according to an embodiment of the present disclosure, the door access control system may further include a visitor counting device configured to count the number of people entering or leaving through the door access control system. For example, if a preset maximum number of people in a room or a building associated with the access control system is 20, then the number for additional people allowed to enter should be subtracted by one every time one person enters. When the count decreases to 0, if someone attempts to enter again, the system may prompt that the number of people inside is full and request the visitor to wait to enter. When someone comes out, the system may detect that a visitor has left, and the count may be increased by one, and so on.

For example, in an application scenario, the doorbell and door access control system may be used for a store, such as a convenience store. The door access control system of the convenience store may include a visitor detection device, such as an image recognition device or an infrared sensing device. When the visitor detection device detects that someone needs to enter, the door access control system may first measure the body temperature of the person about to enter, and issue an alarm when the body temperature exceeds a predetermined threshold, such as 37.3° C., to indicate a risk. In addition, the door access control system may further determine whether there are too many people in the store based on the number of people currently scheduled and the actual number of people in the store associated with the access control system, so as to decide whether to send an alarm signal. That is, according to certain embodiments of the present disclosure, the door access control system may count the number of people entering the store, and control the total number of people in the store according to the number counted. For example, the number of people in the store is added by one each time a person entering the store, and an alarm signal may be issued when the number of people in the store reaches a predetermined threshold. When someone leaves the store, the number of people in the store may be reduced by one accordingly in order to make a more accurate determination when someone wants to enter again later.

There are multiple methods for recognizing the number of visitors, for example, by using 1) image recognition, 2) infrared or laser beam detection for detecting the direction of movement of people, including one or more sets of detectors, and 3) a button on the doorbell configured to open the door and allow one person to enter only when being pressed. The visitor counting device may include one or more of: an image recognition device, a detection device, and a button counter device. The detection device may include an infrared detector or a laser detector. Further the detection device may include at least two sets of infrared detectors or laser detection detectors, and configured to detect the movement direction of the passing people by detecting which set of detectors are passed by first and which set of detectors are passed by later, thereby providing a basis for the current number of people passing through the predetermined area. In an embodiment according to the present disclosure, the button counter device may include a mechanical button or a touch key.

Figure 2:
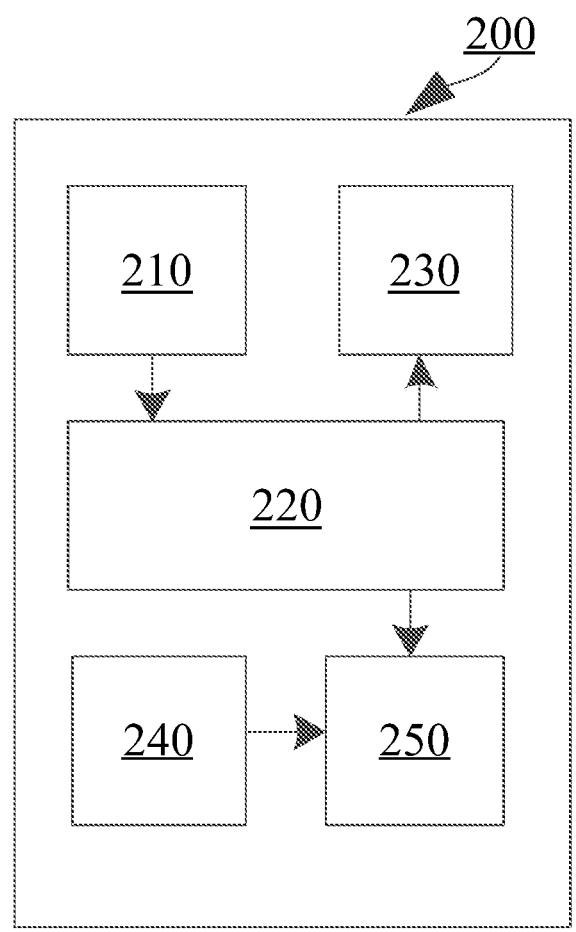
FIG. 2 is a schematic diagram of another door access control system with the body temperature detection function according to some embodiments of the present disclosure.

FIG. 2 is a schematic diagram of a door access control system 200 with the body temperature detection function according to some embodiments of the present disclosure. As shown in FIG. 2, the door access control system 200 with the body temperature detection function includes the following components.

First, the door access control system 200 with the body temperature detection function includes an infrared body temperature monitor device 210. The infrared body temperature monitor device 210 may be configured to detect the body temperature of the monitored object. With the infrared body temperature monitor device 210, the body temperature of a human body close to the infrared body temperature monitor device 210 may be detected to provide the data support for subsequently monitoring the body temperature.

In addition, the door access control system 200 with the body temperature detection function further includes a body temperature comparison device 220. The body temperature comparison device 220 may be configured to compare the detected body temperature of the monitored object with the predetermined body temperature threshold. For example, the general standard to determine fever is 37.3° C., therefore the predetermined body temperature threshold may be set to 37.3° C. Those of skill in the art may know that the 37.3° C. being set here is merely exemplary not restrictive. Other body temperature thresholds related to other diseases may also be used.

Then, the door access control system 200 with the body temperature detection function further includes a warning device 230. The warning device 230 may be configured to issue a warning message when the detected body temperature of the monitored object is higher than the predetermined body temperature threshold.

Further, the door access control system 200 with the body temperature detection function further includes a camera 240. The camera 240 may be configured to obtain an image of a monitored area. As such, the door access control system 200 with the body temperature detection function of the present disclosure may not only report a situation with abnormal body temperature but also capture the image of the monitored area to provide guidance and/or evidence for a subsequent investigation (e.g., epidemiological investigation). In some embodiments, the camera 240 may record a current image when a comparison result of the body temperature comparison device 220 is that the detected body temperature of the monitored object is higher than the predetermine body temperature threshold. Accordingly, the door access control system 200 of embodiments of the present disclosure may not only sense the body temperature of the monitored object but also determine whether to alarm according to the body temperature. In addition, the door access control system 200 further includes the camera 240.

Thus, the door access control system 200 may record image information of the monitored object with the body temperature higher than the predetermine body temperature threshold to provide evidence for subsequent tracking or an epidemiological investigation.

Finally, as shown in FIG. 2, in some embodiments, the door access control system 200 further includes a storage device 250. The storage device 250 may include a local storage device or a cloud storage device.

In addition, in some embodiments, the door access control system 200 may further include a communication device (not shown in FIG. 2). The communication device (not shown in FIG. 2) may be configured to transmit the current image to a target storage device. In some other embodiments, the communication device (not shown in FIG. 2) may be further configured to record time of the current image and the body temperature of the monitored object and store the time and the body temperature in association with the current image. As shown in FIG. 2, the body temperature comparison device 220 may determine that the detected body temperature of the monitored object and the predetermined body temperature threshold may trigger data storage. In this case, the communication device may store the current image with the current time and the detected body temperature captured by the camera 240 in the storage device 250, when the detected body temperature of the monitored object is higher than the predetermined body temperature threshold.

In some embodiments, the target storage device may include the local storage device and/or the cloud storage device. In some embodiments, the communication device may be realized through a wired network connection or a wireless network connection. Accordingly, the door access control system of embodiments of the present disclosure may have a communication device. Thus, the door access control system 200 may not only operate individually as a single device and store all collected information locally but also may be connected to the internet to store the collected information in the cloud to provide a basis for a system including a plurality of door access control systems to perform big data integration. As such, the door access control system 200 may provide evidence for the subsequent tracking or epidemiological investigation.

In some embodiments, the door access control system 200 may further include a power supply device (not shown in FIG. 2). The power supply device (not shown in FIG. 2) may provide power to other components connected to the power supply device in forms of wired and/or wireless power supply. Accordingly, the door access control system of embodiments of the present disclosure may provide power to various components in forms of wired and/or wireless power supply. As such, the door access control system of embodiments of the present disclosure may be implemented flexibly, and the structure of the door access control system of embodiments of the present disclosure may be simplified.

Figure 3:
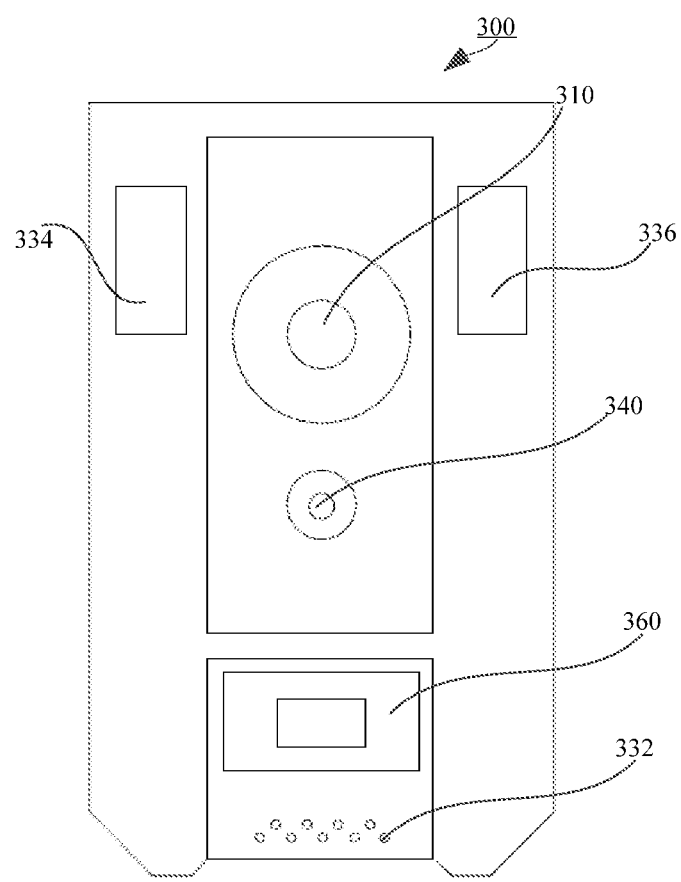
FIG. 3 is a schematic diagram of another door access control system with the body temperature detection function according to some embodiments of the present disclosure.

FIG. 3 is a schematic diagram of a door access control system 300 with the body temperature detection function according to some embodiments of the present disclosure. As shown in FIG. 3, the door access control system 300 with the body temperature monitor function includes the following components.

First, the door access control system 300 with the body temperature monitor function includes an infrared body temperature monitor device 310. The infrared body temperature monitor device 310 may be configured to detect the body temperature of the monitored object. With the infrared body temperature monitor device 310, the body temperature of a human body close to the infrared body temperature monitor device 310 may be detected to provide the data support for subsequently monitoring the body temperature.

In addition, the door access control system 300 with the body temperature monitor function further includes a body temperature comparison device (located in the housing and not shown in FIG. 3). The body temperature comparison device may be configured to compare the detected body temperature of the monitored object with the predetermined body temperature threshold. For example, the general standard to determine the fever is 37.3° C. The predetermined body temperature threshold may be set to 37.3° C. Those of skill in the art should know that 37.3° C. is merely exemplary but not restrictive. Other body temperature thresholds related to other diseases may also be used.

Further, the door access control system 300 with the body temperature monitor function includes a warning device. the warning device may include one or more warning devices 332, 334, or 336. The warning device may be configured to issue a warning message when the detected body temperature of the monitored object is higher than the predetermined body temperature threshold. As shown in FIG. 3, the warning device includes an indicator. When the detected body temperature of the monitored object is higher than the predetermined body temperature threshold, the indicator may emit the red light. When the detected body temperature of the monitored object is not higher than the predetermined body temperature threshold, the indicator may emit the green light.

In some embodiments, the indicator may include a red indicator 336 and a green indicator 334. When the detected body temperature of the monitored object is higher than the predetermined body temperature threshold, the red indicator 336 may be lighted up, and the green indicator 334 may not be lighted up. When the detected body temperature of the monitored object is not higher than the predetermined body temperature threshold, the red indicator 336 may not be lighted up, and the green indicator 334 may be lighted up. Accordingly, the warning signal generated by the warning device may be simply demonstrated in the forms of the red indicator 336 or the green indicator 334. As such, the door access control system 300 of embodiments of the present disclosure may be simple, easy to use, and user friendly.

In addition, in some embodiments, the warning device, for example, may be a loudspeaker 332. The loudspeaker 332 may be configured to issue an alarm buzzer or alarm voice when the detected body temperature of the monitored object is higher than the predetermined body temperature threshold. Accordingly, the warning signal generated by the warning device may be simply demonstrated in the forms of the alarm buzzer or alarm voice. As such, the door access control system 300 of embodiments of the present disclosure may be simple, easy to use, and user friendly.

In addition, as shown in FIG. 3, the door access control system 300 with the body temperature monitor function further includes a camera 340. The camera 340 may be configured to obtain an image of the monitored area. As such, the door access control system 300 with the body temperature monitor function of the present disclosure may not only report the situation with the abnormal body temperature but also capture the image of the monitored area to provide the guidance and/or evidence for the subsequent investigation (e.g., epidemiological investigation). In some embodiments, the camera 340 may record the current image when the comparison result of the body temperature device shows that the detected body temperature of the monitored object is higher than the predetermined body temperature threshold. Accordingly, the door access control system 300 of embodiments of the present disclosure may sense the body temperature of the monitored object and determine whether to issue an alarm according to the body temperature. In addition, since the door access control system 300 further includes the camera 340, the door access control system 300 may further, for example, record the image information of the monitored object with the body temperature higher than the predetermined body temperature threshold to provide evidence for the subsequent tracking or epidemiological investigation.

In addition, as shown in FIG. 3, the door access control system 300 further includes a button 360. When the button 360 is pushed down, the camera 340 record the current image of the monitored area. Accordingly, the door access control system 300 of embodiments of the present disclosure may not only sense the body temperature of the monitored object but also determine whether to issue the alarm according to the body temperature. In addition, since the door access control system 300 may further, for example, record the image information of a person, who requests to open the door, to provide the evidence for the subsequent tracking or epidemiological investigation. Those of skill in the art should know that the button may include the fingerprint recognition function. As such, the fingerprint may be used to recognize whether the person, who touches the button, is the owner.

In some embodiments, the door access control system 300 may further include a driver (not shown in FIG. 3). The driver may be configured to prohibit the door connected to and controlled by the door access control system 300 to open when the detected body temperature of the monitored object is higher than the predetermined body temperature threshold. Accordingly, the door access control system 300 of embodiments of the present disclosure may reject the entry of the person with the high temperature to protect the life and health safety of the owner inside.

In some embodiments, the door access control system 300 may further include the body temperature setting device (not shown in FIG. 3). The body temperature setting device may be configured to set the predetermined body temperature threshold. Accordingly, the door access control system 300 of embodiments of the present disclosure may use the body temperature setting device to set the predetermined body temperature threshold. Therefore, the door access control system 300 of embodiments of the present disclosure may flexibly set the predetermined body temperature threshold based on epidemiological statistics and expertise. As such, the door access control system of embodiments of the present disclosure may become smarter.

In addition, for example, embodiments of the present disclosure may provide a smart doorbell. In some embodiments, the smart doorbell may include a camera, a power supply device, a multi-point infrared body temperature sensor, a WIFI circuit, a main controller, a TF card memory, a button, an indicator, and a microphone. The power supply device may include two AA alkaline batteries, which may supply power to various modules through DC-DC conversion and filtering. The multi-point infrared body temperature sensor may detect and send the body temperature of the visitor to the main controller. The main controller may determine the body temperature of the visitor lower than 37.3° C. as normal, then the indicator of the doorbell may light up green. When the visitor pushes the doorbell, the microphone voice may prompt that the body temperature is normal to allow entry. The main controller may determine the body temperature of the visitor higher than 37.3° C. as abnormal, then the indicator of the doorbell may light up red. When the visitor pushes the doorbell, the microphone voice may prompt that the body temperature is abnormal to not allow entry, and the human face may be photographed and recorded by the camera. If the WIFI connection is abnormal, the doorbell may operate offline and store the human face information of the visitor, the time, the body temperature, the photographed image, and the short video in the local memory. If the WIFI connection is normal, the doorbell may automatically upload the record to the background of the system for storage and processing. For the above-described technical problem, that is, the smart door access control system may only have the function to obtain the image through the camera. However, the user may require the door access control system to detect and record the body temperature of the visitor in addition to obtain and recognize the human face image. The existing door access control system does not have the function of measuring and recording the body temperature for the visitor.

The door access control system may effectively record the body temperature of the visitor and issue the alarm through the solution of the present disclosure to ensure the safety of the owner and prevent the epidemic from spreading. Some application scenarios and operating behaviors of the door access control system under these application scenarios are described below.

Scenario one, the door access control system may have a visitor doorbell function and a body temperature measurement function. First, the infrared temperature sensor may detect the body temperature of the visitor. When the body temperature is lower than 37.3° C., the indicator may light up green. When the visitor pushes the doorbell button, the voice may indicate that the body temperature is normal to allow entry. The door access control system may notify the owner to open the door and record the body temperature of the visitor, the human face information, and visiting time. When the body temperature is higher than 37.3° C., the indicator may light up red. When the visitor pushes the doorbell button, the voice may indicate that the body temperature is abnormal, and no entry is allowed. The door access control system may record the body temperature of the visitor, the human face information, and the visiting time.

Scenario two, the door access control system may have the body temperature monitor function. When a pedestrian passes by the doorbell, the infrared body temperature sensor may detect the body temperature of the pedestrian. If the body temperature of the pedestrian is normal, the indicator may light up green. The door access control system may record the current time and the body temperature of the pedestrian, photograph the human face information, and upload the data to the local storage card and cloud. When the detected body temperature is abnormal, the indicator may light up red. The door access control system may record the current time and the body temperature of the pedestrian, photograph the human face information, and upload the data to the local storage card and cloud.

Scenario three, the door access control system may cooperate with the doorbell to open the door automatically. The smart doorbell may store human face information of family members, neighbors, and friends, and assign different access permissions. By setting the visitor as a family member, if the door access control system recognizes the human face as the family member, and the body temperature is normal, the door access control system may transmit the data to the doorbell to open the door automatically. By setting the visitor as a friend, when the owner allows the visitor to enter, the door access control system may detect that the body temperature may be normal and recognize the human face as the friend, the door access control system may send the data to the doorbell to open the door automatically.

In summary, the smart door access control system of some other embodiments of the present disclosure may further include a high-temperature alarm indicator. The green light may indicate that the body temperature of the monitored object is normal. The red light may indicate that the body temperature of the monitored object is abnormal, and the monitored object is prohibited to enter through the voice alarm. In addition, the smart door access control system of still some other embodiments of the present disclosure may record and report the visiting time of the visitor, the human image of the visitor, and the body temperature data. The smart door access control system may be linked to the electronic lock to automatically open the door for the person with the normal body temperature and not to open the door for the person with abnormal body temperature.

Although different exemplary embodiments of the present disclosure have been described, those skilled in the art should know that various changes and modifications may be made without departing from the spirit and scope of the present disclosure to realize one or some of the advantages of the present disclosure. For those skilled in the art, other components performing the same function may be replaced appropriately. The features explained with reference to a particular drawing may be combined with features of other drawings, even the combination of the features is not explicitly mentioned. In addition, the method of the present disclosure may be implemented either in a software implementation using appropriate processor instructions or in a hybrid implementation using a combination of hardware logic and software logic to achieve the same result. Such modifications to the solution of the present disclosure are intended to be covered by the appended claims.

What is claimed is:

1. A door access control system implemented at a door, in a form of a doorbell, granting or preventing access of a monitored object to a restricted area, the doorbell being with a temperature detection function, the door access control system comprising:
 a body temperature monitor device configured to detect a body temperature of the monitored object, when the monitored object is seeking access to the restricted area;
 a body temperature comparison device configured to compare a detected body temperature of the monitored object with a body temperature threshold;
 a warning device configured to issue a warning message in response to the detected body temperature of the monitored object being higher than the body temperature threshold;
 the door access control system further comprising a first indicator and a second indicator, wherein the first indicator lights up and the second indicator does not light up, in response to the detected body temperature of the monitored object being higher than the body temperature threshold, and wherein the first indicator does not light up and the second indicator lights up, in response to the detected body temperature of the monitored object not being higher than the body temperature threshold; and
 a camera configured to obtain an image of the restricted area after, and in response to, a comparison result of the body temperature comparison device and before the monitored object is granted the access to the restricted area.

2. The door access control system of claim 1, wherein: the warning device includes a visual reminder device configured to issue the warning message in a visual format.

3. The door access control system of claim 1, wherein the warning device includes a red indicator and a green indicator.

4. The door access control system of claim 1, further comprising: a storage device being a local storage device or a cloud storage device.

5. The door access control system of claim 1, further comprising: a button, wherein in response to the button being pushed down, the camera records the image of the restricted area.

6. The door access control system of claim 1, further comprising: a communication device configured to send the image of the restricted area to a target storage device.

7. The door access control system of claim 6, wherein the communication device is further configured to record and store time of the image of the restricted area and the body temperature of the monitored object.

8. The door access control system according to claim 1, further comprising: a query interface device configured to query visitor information of visitors meeting a predetermined condition.

9. The door access control system according to claim 8, wherein the predetermined condition includes one or both of: a predetermined period of time; and a predetermined temperature threshold.

10. The door access control system according to claim 8, wherein the visitor information includes one or more of: images of the visitors; time; a number of the visitors; and a body temperature.

11. The door access control system of claim 1, wherein the warning device includes: a loudspeaker configured to issue an alarm buzzer or an alarm voice in response to the detected body temperature of the monitored object being higher than the body temperature threshold.

12. The door access control system of claim 1, further comprising: a driver configured to prohibit a door connected to and controlled by the door access control system to open in response to the detected body temperature of the monitored object being higher than the body temperature threshold.

13. The door access control system according to claim 1, further comprising: a visitor counting device configured to count a number of people entering or leaving through the door access control system.

14. The door access control system according to claim 13, wherein the visitor counting device includes one or more of: an image recognition device; a detection device; and a button counter device.

15. The door access control system according to claim 14, wherein: the detection device includes one or both of an infrared detector and a laser detector.

16. The door access control system according to claim 15, wherein the detection device includes one or both of an infrared detection detector and a laser detector.

17. The door access control system according to claim 1, wherein the body temperature monitor device is positioned between the first indicator and the second indicator.

18. The door access control system according to claim 1, wherein the doorbell stores human face information of a family member, a neighbor, or a friend.

19. The door access control system according to claim 18, wherein the doorbell assigns a first access permission to the family member, a second access permission to the neighbor, and a third access permission to the friend, and wherein the third access permission is different than the first access permission or different than the second access permission.

* * * * *